United States Patent [19]

Noll et al.

[11] Patent Number: 4,968,437

[45] Date of Patent: Nov. 6, 1990

[54] FLUID PURIFICATION SYSTEM

[75] Inventors: John R. Noll, Middlebury; Stephen V. Montvila, Brookfield, both of Conn.

[73] Assignee: Electrolux Water Systems, Inc., Marietta, Ga.

[21] Appl. No.: 183,658

[22] Filed: Apr. 19, 1988

Related U.S. Application Data

[63] Continuation of Ser. No. 915,238, Oct. 3, 1986, Pat. No. 4,769,131, which is a continuation-in-part of Ser. No. 861,569, May 9, 1986, abandoned.

[51] Int. Cl.$^5$ .................. G01N 23/10; G01N 23/12
[52] U.S. Cl. .................................. 210/748; 204/152; 204/186; 210/223
[58] Field of Search .............. 210/195.1, 259, 295, 210/748, 222, 223; 422/24, 119; 250/435–438, 504; 204/149, 152, 186

[56] References Cited

U.S. PATENT DOCUMENTS

| | | | |
|---|---|---|---|
| 1,151,267 | 8/1915 | Helbronner et al. | 422/24 |
| 2,968,734 | 1/1961 | Yeomans | 250/106 |
| 3,276,458 | 10/1966 | Iversen et al. | 210/259 |
| 3,519,817 | 7/1970 | Brunner | 250/436 |
| 3,550,782 | 12/1970 | Veloz | 210/192 |
| 3,814,680 | 6/1974 | Wood | 422/24 |
| 3,894,236 | 7/1975 | Hazelrigg | 250/435 |
| 4,151,085 | 4/1979 | Malik | 210/101 |
| 4,204,956 | 5/1980 | Flatow | 422/119 |
| 4,400,270 | 8/1983 | Hilman | 422/24 |
| 4,798,702 | 1/1989 | Tucker | 210/748 |

Primary Examiner—Frank Sever
Attorney, Agent, or Firm—McAulay Fisher Nissen & Goldberg

[57] ABSTRACT

A fluid purification system includes an elongated ultraviolet radiation emitting tube and independent fluid flow-controlling conduits. Each conduit is transparent to allow ultraviolet light emitted by the tube to enter the conduit, and defines a continuous, and is helically wound closely about the tube to insure that fluid flow through the conduits is exposed to the ultraviolet light. The system includes a filter having inlet and outlet ports. An end of each conduit is connected to one of the inlet and outlet ports of the filter. The system thus exposes the fluid to ultraviolet radiation both before and after the fluid is filtered.

17 Claims, 6 Drawing Sheets

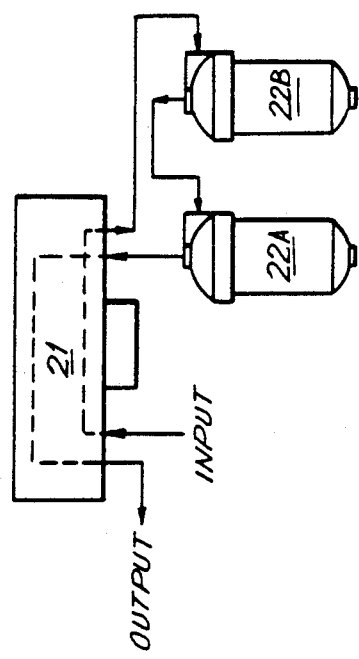
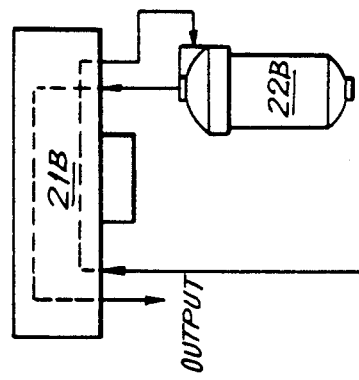
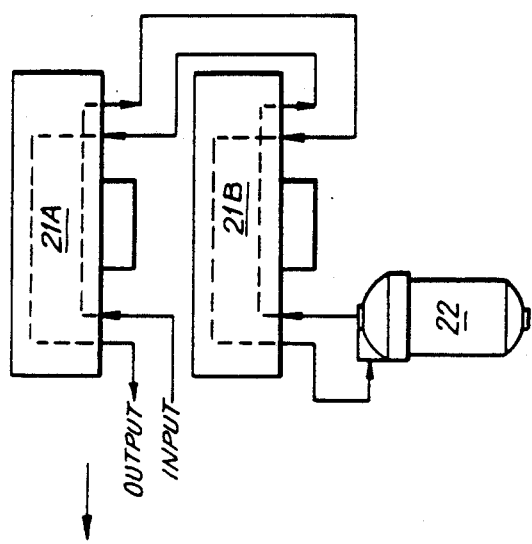
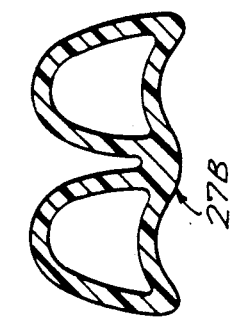
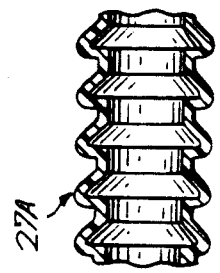
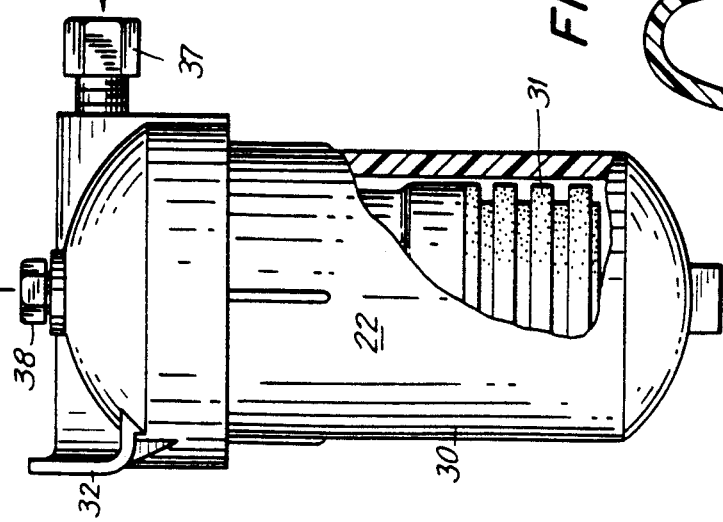

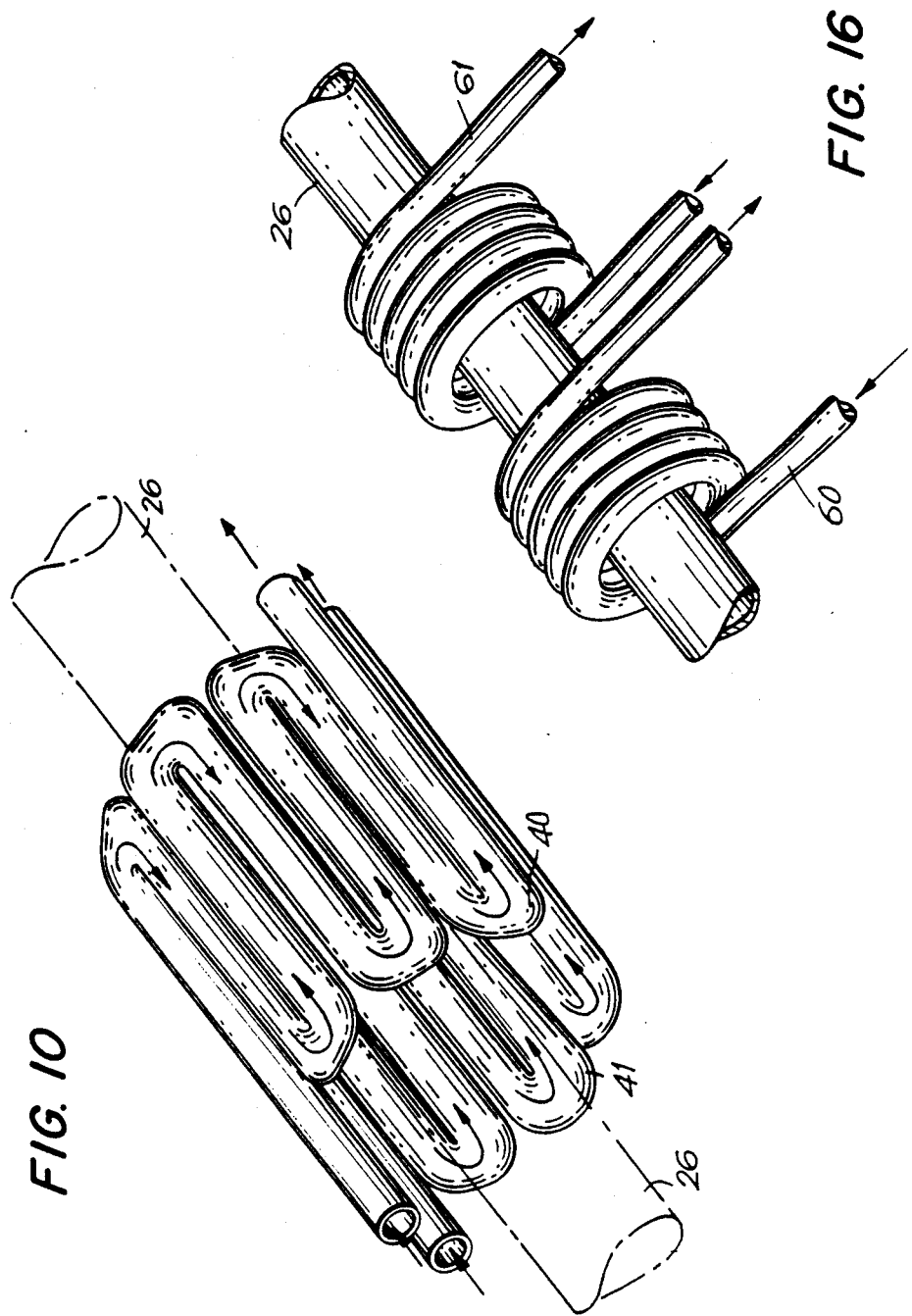

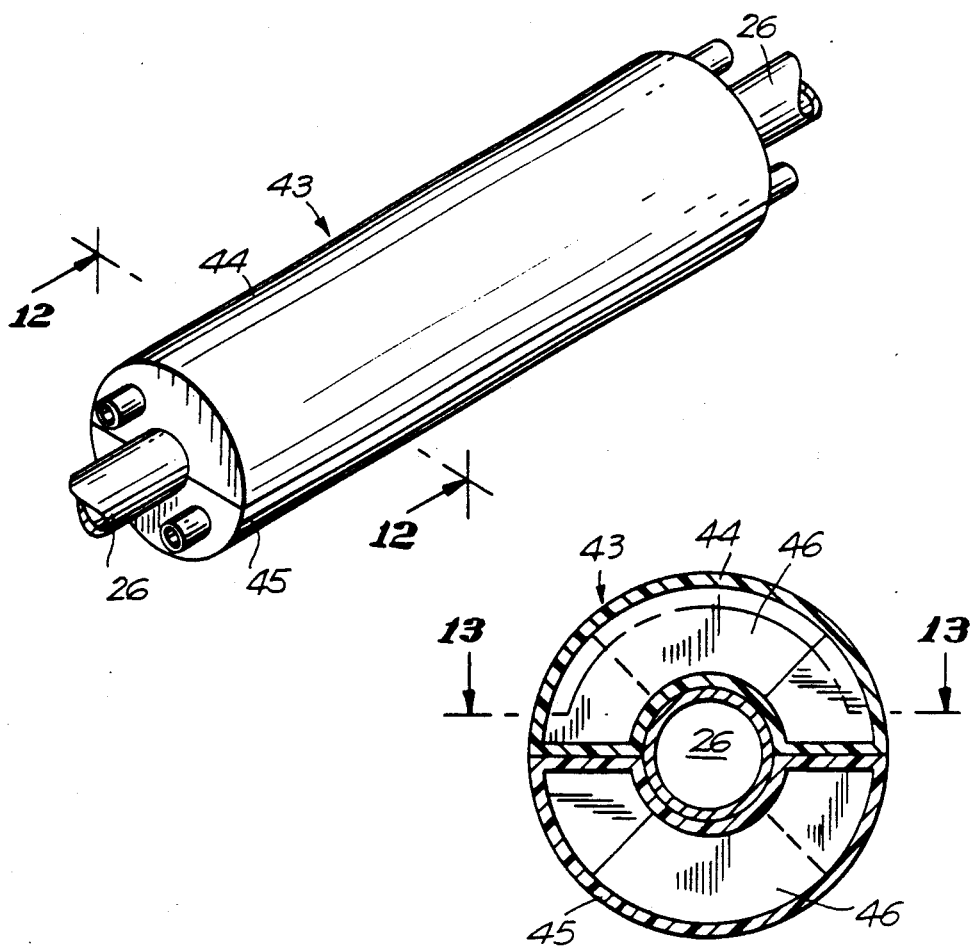
FIG. 11
FIG. 12
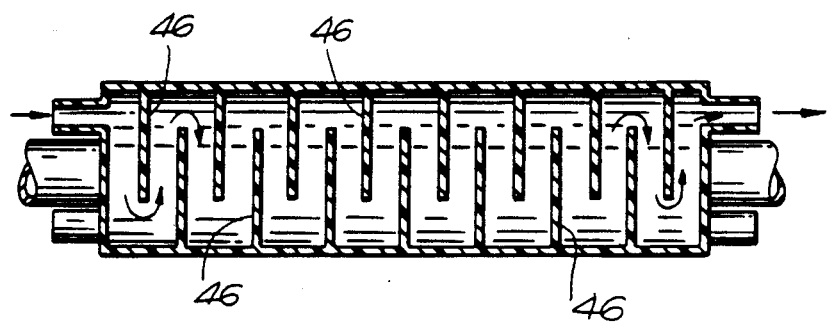
FIG. 13

FLUID PURIFICATION SYSTEM

This is a continuation of application Ser. No. 915,238, filed Oct. 3, 1986, now U.S. Pat. No. 4,769,131, which is a continuation-in-part of Ser. No. 06/861,569, May 9, 1986, now abandoned.

BACKGROUND OF THE INVENTION

1. Field of the Invention

This invention relates to fluid purification systems and more particularly to fluid purification systems incorporating fluid exposure to both ultraviolet radiation and filtration.

2. Description of the Prior Art

In an attempt to provide high quality, potable drinking water, various treatment systems have been developed. Many such systems employ activated carbon filters, as a common treatment to remove odor, improve taste, and remove chemicals, such as chlorine and chloroforms. However, carbon is a nutrient source that supports bacteria life and growth. As a result, unless these filters are replaced frequently, the filters themselves provide a breeding ground for bacterial contamination. This bacteria is spread to the consumer as the water flows through the filter, picking up the bacterial contamination and delivering the bacteria to the user.

It has been found that activated charcoal filters are so conducive to bacterial growth that filters not routinely replaced may provide more bacterial contamination to the water than the unfiltered water itself. In addition, the bacteria tend to occupy many of the absorptive sites in the filter, reducing the filter's absorptive capacity and rendering the filter ineffective for its intended purpose of purifying the water.

It is well known that exposure of water to ultraviolet radiation kills microorganisms and bacteria carried by the water. For this reason, many conventional purification systems employ an ultraviolet sterilization unit in series with a filtration unit.

For example, U.S. Pat. No. 3,550,782 to Veloz discloses a water sterilizer apparatus having a pair of parallel water carrying tubes, and a string of ultraviolet bulbs located between the tubes. A reverse osmosis unit is connected in series between the tubes, so that the water flowing through the tubes is exposed to ultraviolet radiation both upstream and downstream of the reverse osmosis unit. The Veloz '782 patent states that the destruction of bacteria upstream of the reverse osmosis unit is desirable in order to protect the membrane of the unit against the accumulation of live bacteria. The filtered and sterilized water is stored in a large tank, from which water is drawn on demand.

The apparatus disclosed in the Veloz '782 patent may be suitable for some applications, but is impractical for home, domestic use.

First, the tank used in the Veloz system may act as a further breeding ground for microorganisms and bacteria, especially if the water remains in the tank for any extended period of time. The tank is connected to the faucet or water outlet, and bacteria may enter the tank through the faucet. Also, the tank may require periodic flushing or cleaning, to remove bacteria laden water as well as sediment and the like. Furthermore, unless the tank is pre-sterilized prior to its use, or sterilized periodically during use (which would be an almost impossible task for the consumer to undertake), any water fed to the tank from the sterilizer unit would quickly become contaminated with bacteria.

Second, the Veloz apparatus employs straight-line liquid flow tubes adjacent to the string of ultraviolet bulbs. Such a straight-line configuration is impractical for installation in a private residence.

Size constraints of a home installed purification system are of paramount importance. A purification system for use in a private residence should be a compact unit, easily installable by the consumer, within a kitchen sink cabinet or a bathroom vanity, for example.

The storage tank of the apparatus disclosed in the Veloz '782 patent requires an inordinate amount of space. Furthermore, if the storage tank were omitted from the Veloz system and the water was drawn on demand directly from the downstream tube, each tube would necessarily be of such length that it would be impractical to install the system in a private home.

For example, assuming that the average flow rate of water consumed in a private residence is one gallon per minute, and assuming that the string of bulbs provide an average of 90,000 microwatt seconds per square centimeter of ultraviolet radiation, then each tube of the Veloz sterilization unit would have to be at least 6 feet long, with a cross sectional area of 0.2 square inches, to effectively kill the bacteria and microorganisms carried by the water.

In addition, the apparatus disclosed in the Veloz '782 patent is not maximally effective in sterilizing the water and maintaining the reverse osmosis filtration unit in a bacteria free state. This is believed to be due to the straight-line path of the water through the flow tubes, which provide no turbulence to the water flow.

OBJECTS AND SUMMARY OF THE INVENTION

It is a principal object of the present invention to provide a water purification system which is an improvement over the apparatus disclosed in U.S. Pat. No. 3,550,782, and which overcomes the inherent disadvantages of that system.

It is another object of the present invention to provide a water purification system which is capable of providing high quality, purified, potable water which is substantially free of all living microorganisms as well as free of substantially all particulate matter and undesirable chemicals.

It is still another object of the present invention to provide a water purification system having the characteristic features described above which is easily installed for domestic use, and inexpensive to purchase and operate.

It is a further object of the present invention to provide a water purification system having the characteristic features described above which is capable of easily being expanded or configured to satisfy any particular need.

It is yet another object of the present invention to provide a water purification system having the characteristic features described above which is constructed for maximum water purification in a minimum-sized unit.

It is a still further object of the present invention to provide a water purification system having the characteristic features described above which combines ultraviolet radiation exposure and filtration in a manner which minimizes bacterial growth in the filter medium.

It is yet another object of the present invention to provide a water purification system having the characteristic features described above which substantially eliminates the delivery of system generated bacterial contamination to the user.

It is a further object of the present invention to provide a water purification system having the characteristic features described above which is extremely efficient in its operation.

In one form of the present invention, a fluid purification system includes two independent fluid flow-controlling conduits, each of which defines an independent fluid flow channel, which are spirally wound about a substantial portion of an elongated, ultraviolet radiation producing tube. Each of these conduits is made from an ultraviolet permeable material, so that the fluid flowing through the conduits will be exposed to ultraviolet radiation emitted by the ultraviolet tube. Furthermore, both of these fluid flow-controlling conduits are connected to a filter, with one conduit being connected to the inlet of the filter and the other conduit being connected to the outlet of the filter.

The circuitous path of the fluid flowing through the spirally wound conduits creates a turbulent flow, which ensures exposure of all of microorganisms carried by the water to ultraviolet radiation. Furthermore, spirally winding the conduits allows them to be tightly packed, which decreases the overall length of the ultraviolet tube required for sufficient exposure. Thus, the fluid purification system of the present invention assures that the water entering the filter is maximally exposed to ultraviolet radiation prior to filtration, as well as being maximally exposed to ultraviolet radiation a second time, after passage through the filter. It has been found that the configuration described above provides a water purification system which overcomes many disadvantages inherent in conventional purification systems, and attains a water delivery system capable of producing dependable, continuous, reliable potable water, virtually free of live microorganisms, particulate matter, chemicals, and odor. In addition, the system is equally useful for all fluids in which contaminant purification is sought.

The present invention attains maximum ultraviolet radiation exposure with the equipment being held to the minimum size. As a result, a system capable of providing high quality, potable water, or other fluid, virtually free of bacteria, particulate, and chemicals is attained, with its overall size being sufficiently small to be easily mounted in any domestic situation in direct association with any desired water faucet or other fluid source.

By employing the present invention, it has been found that bacterial growth in the filter medium is virtually eliminated. It is believed that the present invention completely eliminates the food supply for the microorganisms in the filter medium.

In the present invention, the fluid flowing through the system is exposed to ultraviolet radiation prior to entering the filtration zone. This kills most, if not all, live microorganisms in the fluid prior to their reaching the filter. Furthermore, upon exiting the filter, a second exposure of ultraviolet radiation is provided. In this way, any microorganisms which may have passed through the first exposure or which have been retained in the filter medium are killed prior to delivery of the fluid for use or consumption.

In addition, passage of airborne microorganisms into the filter medium entering through the fluid delivery port is prevented, since all bacteria or microorganisms would have to pass through the ultraviolet radiation prior to reaching the filtration zone. Consequently, the food supply for any microorganisms retained in the filter zone is cut off, due to the dual exposure of ultraviolet radiation, and the filter medium is maintained substantially bacteria free.

A further feature of the present invention is the modularization of the purification system of this invention into a sterilization section and a filtration section. In this way, additional sterilization sections and additional filtration sections can be combined in any desired configuration to customize a purification system for various unique situations.

For example, if specific microorganisms, such as giardia lamblia, which are resistant to ultraviolet radiation, were known to be contaminating the water supply, additional sterilization sections would be added to the purification system to provide the necessary ultraviolet exposure to assure that a high quality potable water product is attained. Similarly, if particular toxic chemicals were known to be in the water supply, additional filter sections would be added to the purification system to remove these toxic chemicals and provide the desired high quality potable water.

Preferred forms of the water purification system, as well as other objects, features and advantages of this invention, will become apparent from the following detailed description of illustrative embodiments thereof, which is to be read in connection with the accompanying drawings.

BRIEF DESCRIPTION OF THE DRAWINGS

FIG. 4 is a side elevational view, partially broken away, showing the filter section of the fluid purification system shown in FIG. 1.

FIGS. 5, 6 and 7 are schematic views showing various structural arrangements in which the modularized fluid purification system of this invention can be employed.

FIGS. 8 and 9 are schematic, cross-sectional views showing alternate configurations for the fluid flow-controlling conduit means employed in the fluid purification system of this invention.

FIG. 10 is a perspective view of an alternative, second embodiment of the present invention.

FIG. 11 is a perspective view of a third embodiment of the present invention.

FIG. 12 is a sectional view of the embodiment shown in FIG. 11 taken along the lines 12—12 of FIG. 11.

FIG. 13 is a sectional view of the embodiment shown in FIG. 11 taken along the lines 13—13 of FIG. 12.

FIG. 16 is a perspective view of a fifth embodiment of the present invention.

DETAILED DESCRIPTION OF THE PREFERRED EMBODIMENTS

Figure 1:
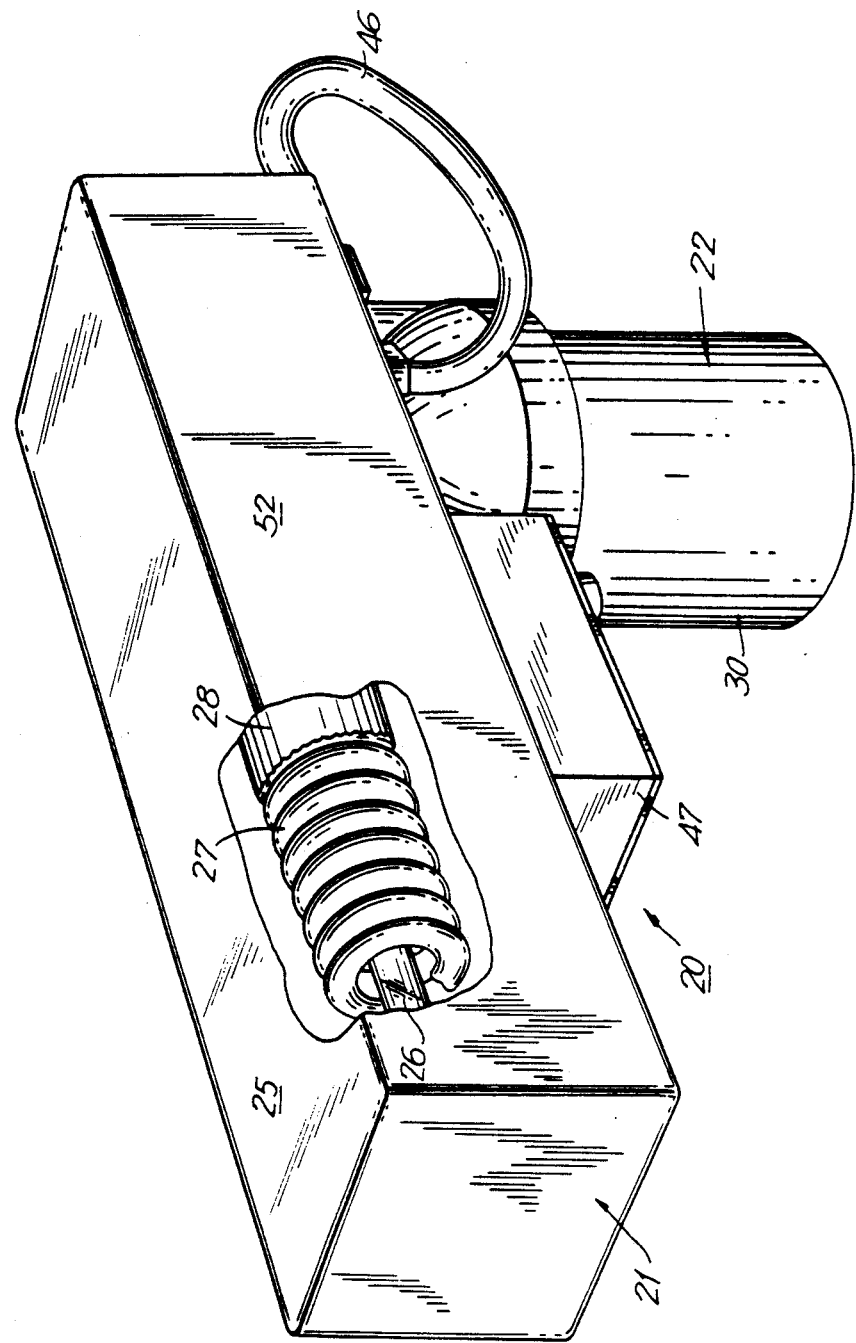
FIG. 1 is a perspective view, partially broken away, showing one preferred form of the fluid purification system of this invention.

In FIG. 1, one preferred embodiment of fluid purification system 20 of the present invention is shown. In this embodiment, system 20 comprises a sterilization section 21 and a filter section 22.

Sterilization section 21 incorporates a housing 25 in which an elongated, ultraviolet radiation producing tube 26 is securely mounted and connected to electronic control means (not shown) to assure continuous production of ultraviolet radiation. In addition, in this preferred embodiment, fluid flowcontrolling conduit means 27 are arcuately coiled about elongated tube 26 in juxtaposed, spaced radiation receiving relationship therewith. As will be described in more detail, conduit means 27 includes first and second ultraviolet radiation transmissible portions, which define first and second flow channels, respectively, for the passage of the fluid in tortuous paths about the periphery of tube 26, and which further define a fluid inlet and a fluid outlet for each of the first and second flow channels. Conduit means 27 controls the fluid flow about tube 26 and assures that the fluid flowing therethrough receives the requisite exposure to ultraviolet radiation.

Preferably, a radiation reflective shield 28 peripherally envelopes conduit means 27, in order to maximize the effectiveness of the ultraviolet radiation as well as prevent or reduce the radiation reaching the outside area. Typically, due to its ease of installation, any reflective material which comprises a cylindrical shape or is easily formed into a cylindrical shape is used for shield 28.

In the embodiment depicted in FIGS. 1 and 4, filter section 22 incorporates a housing 30, in which filter means 31 is securely retained and positioned. Furthermore, housing 30 incorporates bracket means 32, to securely affix filter section 22 to sterilizer section 21.

As is more fully detailed below, depending upon the particular contamination contained in the fluid being purified, filter means 31 comprises one or more of the following filter elements—particulate matter filtration, odor filtration, organic chemical filtration, etc. Typically, filter means 31 comprises an activated charcoal filter to improve water taste by removing undesirable chemicals and suspended particles. However, any other type of filter may be employed, either individually or in combination, in order to satisfy any particular requirement.

Figure 2:
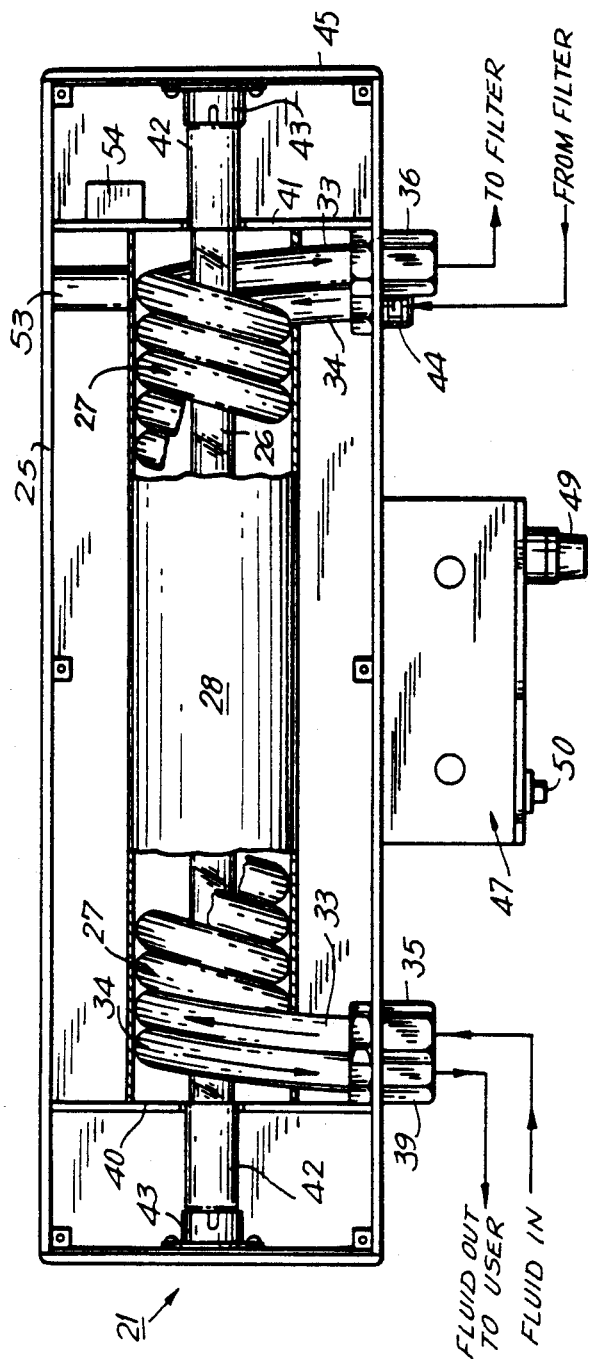
FIG. 2 is a side elevational view of the sterilizer section of the fluid purification system shown in FIG. 1, with the side cover removed therefrom.
Figure 3:
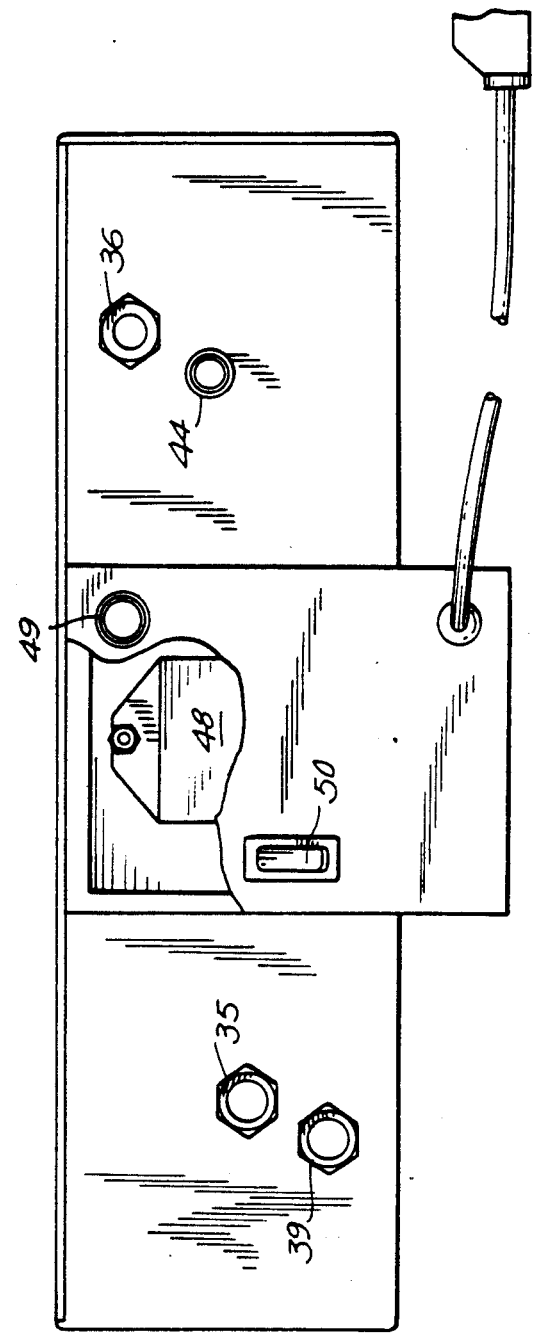
FIG. 3 is a bottom plan view of the sterilizer section of the fluid purification system shown in FIG. 1.

As depicted in FIGS. 1, 2 and 3, one preferred embodiment of fluid flow controlling conduit means 27 comprises two, transparent substantially equal length tube members 33 and 34, each of which are spirally wound about elongated, ultraviolet radiation producing tube 26 in direct, juxtaposed, spaced facing relationship therewith, extending along substantially the entire length thereof. Preferably, the tube members 33 and 34 are interleaved with each other, with each coil of tube member 33 being adjacent to a coil of tube member 34. Although alternate configurations for the fluid carrying conduit means 27 are shown in FIGS. 10 to 15 and will be described in detail, the arcuately coiled embodiment depicted in FIGS. 1 and 2 is preferred for maximizing the exposure of the fluid travelling through the conduit means to ultraviolet radiation, using a minimum tube length and a minimum overall system size.

Another principal aspect of the present invention is the construction of fluid purification system 20 with one of the two portions of the fluid flow controlling conduit means 27 being employed to carry the fluid entering the system through a first exposure to ultraviolet radiation, followed immediately by passage of the fluid through filter 31 of filtration section 22. In addition, once the fluid has passed through filter 31, the fluid enters the other portion of the fluid flow controlling conduit means 27 for a second ultraviolet radiation exposure. Once this second exposure is completed, the purified fluid is delivered directly to the outlet faucet or portal for immediate use.

In FIGS. 1, 2, 3 and 4, this preferred construction is shown with tube means 33 receiving the input fluid flow through portal/fitting 35 and controllably carrying the fluid about the arcuately coiled flow path defined thereby, assuring that the fluid flowing therethrough is continuously exposed to the ultraviolet radiation emanating from tube 26. Upon reaching portal/fitting 36, which is the output of tube means 33, the fluid is carried through a connecting tube 46 to filter input portal/fitting 37.

Once the fluid has thoroughly circulated through filter means 31 of filter section 22, the filtered fluid is delivered to portal/fitting 38, and delivered therefrom to portal/fitting 44, which is the input portal to tube means 34. Preferably, exit portal/fitting 38 of filter section 22 and input portal/fitting 44 of tube means 34 are constructed for mating engagement. However, interconnecting tube means may be employed if desired.

Once in tube means 34, the fluid advances through the arcuately coiled flow path defined by tube means 34, wherein the fluid is exposed to the ultraviolet radiation a second time, as the fluid again arcuately flows along the length of elongated ultraviolet radiation tube 26, continuously advancing while simultaneously peripherally circulating thereabout. Once the fluid has passed through tube means 34, the fluid exits through portal/fitting 39 for direct delivery to the user.

Preferably, the purified fluid exiting portal 39 is delivered directly to a faucet or other suitable means for immediate use. By eliminating the need for a storage or holding tank, such as used in the apparatus disclosed in U.S. Pat. No. 3,550,782, wherein bacterial contamination would flourish, the purity of the fluid delivered to the user of the present invention is assured.

It has been found that by employing the present invention, purified fluid is obtained which is substantially free of all bacteria, organic contaminants, particulates, odors, and other common, undesirable contaminants. Furthermore, it has been found that by employing the purification system 20 of this invention, filter longevity is attained and contamination and bacterial breeding in the filter is virtually eliminated.

In order to determine the overall size that the fluid purification system of the present invention must be to attain a purified fluid, substantially free of all live microorganisms, several factors must be considered. First of all, the flow rate of the fluid passing through the system must be established and, secondly, for the given flow rate, the total amount of ultraviolet radiation exposure required must be established.

In determining the ultraviolet radiation exposure required, the type of fluid to be purified and the microorganisms commonly found in that fluid are established. For this analysis, typical drinking water has been selected as the fluid, with the water containing contaminants typically encountered with drinking water. However, the resistance of various microorganisms found in drinking water must be known.

In general, most bacteria are killed by exposures to ultraviolet radiation ranging between about 16,000 and 20,000 microwatt seconds per square centimeter. In addition, viruses commonly found in drinking water supplies are killed by ultraviolet radiation exposures ranging between about 6,000 and 40,000 microwatt seconds per square centimeter. Mold spores require up to 60,000 microwatt seconds per square centimeter in order to be killed, while parasites may require up to 200,000 microwatt seconds per square centimeter or more of ultraviolet radiation before such parasites are killed. In view of these statistical averages, a design objective of 90,000 microwatt seconds per square centimeter was established as the total ultraviolet radiation exposure to which the water passing therethrough should be exposed. However, if desired, a higher exposure can be attained in a variety of ways, such as reducing the flow rate or adding sterilizing sections, as detailed herein.

With this exposure rate established, the water flow rate was determined. Since a flow rate of one gallon per minute is practical for most domestic water sources, this rate was employed to establish the overall size of sterilization section 21 of fluid purification system 20.

Using these criteria, along with the known output of ultraviolet radiation producing tubes, it was found that each tube member 33 and 34 should have a length of at least 6 feet with a cross-sectional area of about 0.2 square inches. With these design goals in mind, it was established that an ultraviolet radiation producing tube having an overall length of 15 inches, with an illuminated area of about 13.5 inches, provided the desired axial length for accommodating the preferred lengths of interleaved, spirally wound tube members 33 and 34.

As shown in FIGS. 1, 2 and 3, the preferred embodiment of sterilizing section 21 of fluid purifying system 20 also incorporates tube supporting walls 40 and 41, which peripherally surround and supportingly retain a portion of the mounting ends 42 of ultraviolet radiation producing tube 26. As is well known in the art, ends 42 of tube 26 incorporate prong contacts extending therefrom, which are interconnected with support plugs 43 mounted to housing 25, providing the required electrical connection.

In addition, in this preferred embodiment, front wall 45 is removably attached to housing 25 by screw means. In this way, wall 45 can be easily removed, whenever necessary in order to change ultraviolet radiation producing tube 26. Once wall 45 has been disconnected from housing 25, one end of tube 26 is automatically disconnected and can be quickly and easily removed from supporting engagement with walls 40 and 41 and then replaced by a new tube. In this way, the efficient operation of sterilization section 21 of this invention can be easily maintained.

If desired, housing 25 may incorporate a removable side wall panel 52. In this way, access to the interior of housing 25 would be easily attained.

In the preferred embodiment, all of the electronics required to operate sterilizing section 21 are mounted directly below housing 25, preferably nested within supporting bracket assembly 47. As shown in FIGS. 2 and 3, included within bracket assembly 47 is a transformer 48 which controls the requisite voltage output for properly driving the ultraviolet radiation producing tube 26. In addition, fuse means 49 and an on/off power control switch 50 are included. Any other desired electronics could be incorporated in this zone, including such other optional items as light means (not shown) for providing a positive illumination indication that the system is turned on and properly powered.

Bracket assembly 47 is mounted to the lower wall of housing 25 of sterilizer section 21. In the preferred embodiment, bracket assembly 47 comprises a side wall in which holes are formed in order to facilitate the installation of fluid purifying system 20 of the present invention to an abutting support wall. If desired, mounting holes may be formed in the opposed wall of bracket assembly 47, or bracket assembly 47 may be mounted with the mounting hole containing portion thereof aligned with either the right side or the left side of housing 25 of sterilization section 21. In this way, a universally adaptable mounting system is achieved.

In another preferred embodiment, fluid purifying system 20 of the present invention incorporates ultraviolet radiation level sensing means and cooperating alarm means, in order to inform the user whenever the level of ultraviolet radiation falls below the level required to kill the microorganisms passing therethrough. Preferably, ultraviolet radiation sensing means 53 is mounted directly adjacent on of the fluid flow controlling conduit means 27. This position is preferred since, in this way, sensor 53 senses both the ultraviolet radiation output of tube 26, as well as the amount of ultraviolet radiation passing through fluid flow-controlling conduit means 27.

In addition, sensor means 53 is connected to an alarm means 54, in order to provide a positive, recognizable indication to the user that a fault condition exists. Alarm means 54 may comprise a sound producing device, such as a horn or bell, in order to audibly warn the user that a fault condition exists. If desired, alarm means 54 may comprise visual indicating means, such as a light, which is illuminated or constructed to flash whenever a fault condition is found. Furthermore, a combination of both alarm types could be employed.

Although ultraviolet radiation sensor 53 may be positioned directly adjacent to ultraviolet radiation producing tube 26, the preferred position is directly adjacent to one of the fluid flow-controlling conduit means 27. This position is preferred since, in this way, sensor 53 will sensor both a reduction in the ultraviolet radiation produced by tube 26, as well as a reduction in the ultraviolet radiation passing through fluid flow-controlling conduit means 27. As a result of this construction, in addition to reduced output from tube 26, a fault condition will be recognized and identified if the fluid passing through fluid flow-controlling conduit means 27 comprises a colloidal suspension or other concentrated particulate matter which prevents the requisite level of ultraviolet radiation from passing through conduit means 27.

This is particularly important when the system is installed to purify drinking water, since heavily soiled, or particle-laden water may not be capable of being completely purified using the sizing of the system constructed for conventional water sources. With this system, the user is provided with a positive indication that the fluid passing through purifying system 20 has an abnormal condition which might be incapable of being fully purified.

In the preferred embodiment, fluid sterilization system 20 of the present invention is constructed with sterilizer section 21 and filter section 22 being completely modularized, in order to allow any desired configuration or component interconnection required for specific application requirements. In FIGS. 2 and 3, sterilizer section 21 is depicted in detail, as described above, with the section being constructed for ease of use as a separate, modular element.

In FIG. 4, a detailed view of filter section 22 is shown, with housing 30 peripherally surrounding and containing removable filter element 31 clearly shown therein, with section 22 constructed for ease in use of any particular desired construction or arrangement.

In FIGS. 5-7, various alternate configurations of the modularized system of this invention are shown. In FIG. 5, two sterilizer sections 21A and 21B are shown cooperatingly interconnected with a single filter section 22. A system of this nature would provide ultraviolet radiation exposure of about 180,000 microwatt seconds per square centimeter, thereby being capable of assuring the elimination of most known bacteria, viruses, spores, and parasites. As a result, in a particular application where high levels of bacteria are present or well known, more resistant microorganisms have been detected, a system as shown in FIG. 5, with two sterilizing sections being employed, would provide the desired fluid purification.

In FIG. 5, the preferred interconnection method for the dual sterilizer sections is shown. As depicted, the fluid entering sterilizer section 21A makes its first pass through section 21A, exits sterilizer section 21A and enters sterilizer section 21B. Once in sterilizer section 21B, the fluid makes its first pass through sterilizer section 21B and passes from sterilizer section 21B into filter 22. After passage through filter 22, the fluid passes for a second time through sterilizer section 21B, followed by a second pass through sterilizer section 21A, where the purified fluid then exits for delivery to the user.

By employing this configuration, the fluid is exposed to a double dose of ultraviolet radiation both before filtration and after filtration. However, if for any particular purpose maximum exposure of the fluid to ultraviolet radiation prior to filtration is considered desirable, this dual sterilizer configuration could be constricted to allow the fluid to pass through sterilizer section 21A in both directions, prior to entering sterilizer section 21B, where a third exposure to ultraviolet radiation would be realized prior to passage of the fluid to filter section 22. Of course, other arrangements can also be employed, as the system may be expanded to include any number of sterilizer sections required to meet particular needs.

In FIG. 6, an alternate arrangement for the modularized fluid purification system 20 of the present invention is shown. In this configuration, a single sterilizing section 21 is employed in combination with two filter sections 22A and 22B. A system construction of this nature is employed in particular installations where a single filter has proven incapable of eliminating the particulate matter, odor, chloroform, or other organic or chemical contents which exists in the fluid supply. In addition, a system of this nature is employed where two different types of filters, such as one activated charcoal and a paper type filter, are required to meet specific needs.

As shown in FIG. 6, the preferred arrangement of this embodiment brings the fluid supply into sterilizer section 21 and then directly from sterilizer section 21 into filter 22A. After passage through filter 22A, the fluid passes into filter 22B for filtration therethrough. Once through filter 22B, the fluid returns to sterilizer section 21 for its final sterilization exposure before being delivered directly to the user.

If desired, additional filters can be mounted to this system, in a similar fashion, in order to provide further filtration of the fluid for particular needs. However, regardless of the number of filters employed, a final passage of the fluid through sterilizer section 21 prior to delivery to the user is required, in order to attain the beneficial aspects of the present invention.

In FIG. 7, a final example of various alternate installations for fluid purification system 20 of the present invention is shown. In this configuration, two sterilizer sections 21A and 21B are employed along with two filter sections 22A and 22B. Although these sections could be interconnected with each other in a variety of alternate ways, without departing from the scope of the present invention, FIG. 7 depicts the particular configuration considered to be preferred. However, regardless of the particular configuration employed, it is important to note that in accordance with the present invention, the fluid must be exposed to ultraviolet radiation prior to filtration, and must be exposed to ultraviolet radiation again after the final filtration, just prior to passage to the user.

The preferred construction shown in FIG. 7 essentially represents the use of two single filtration systems 20, as detailed above, which are connected in series. As shown in FIG. 7, fluid passes through sterilization section 21A, then through filter section 22A, back through sterilization section 21A, as is done with a single fluid purification system 20. However, in this construction, the fluid exiting sterilization section 21A passes through sterilization section 21B and then through filter 22B. Once through filter 22B, the fluid makes a final pass through sterilization section 21B and is then delivered directly to the user.

As is readily apparent from the alternate structural arrangements detailed above for constructing a fluid purification system in accordance with the present invention, these particular constructions are merely examples of numerous alternate construction arrangements that can be employed for the present invention. Consequently, the constructions detailed above have been presented merely for exemplary purposes, and are not in any way intended to limit the scope of the present invention.

In FIGS. 8 and 9, two alternate configurations for the fluid flow-controlling conduit means are shown. In FIG. 8, conduit means 27A is depicted as a corrugated elongated, continuous tube, with the side walls thereof comprising a corrugated, varying diameter configuration along the entire length thereof. It is believed that this corrugated conduit configuration acts optically to enhance the transfer of ultraviolet radiation to the fluid passing therethrough by dispersing the ultraviolet rays, due to the irregular shape of the sidewalls of the corrugated tube.

In FIG. 9, another alternate construction for conduit means 27 is shown. In this configuration, the conduit means 27 comprises an elongated, extruded construction in which two conduits are extruded in a side-by-side configuration, in order to further enhance the construction of sterilizer section 21. Furthermore, in this configuration, the extruded conduit means 27B comprises a convex outer surface matingly interconnected with a concave outer surface. With this configuration, the concave surface is positioned about elongated, ultraviolet radiation producing tube 26 in juxtaposed, spaced facing relationship therewith. In this way, the concave surface functions as a lens, and optically acts to deliver improved ultraviolet radiation transfer to the fluid passing therethrough.

In addition to these two alternate conduit means, a variety of other conduit means constructions can be employed. without departing from the scope of this invention. However, regardless of the tube configuration, the tube or conduit means must be formed from a material or a combination of materials which allows ultraviolet radiation to pass through at least the radiation receiving walls thereof and into the fluid stream. Presently, ultraviolet permeable tubes formed from teflon are preferred. However, any other material having similar or better ultraviolet radiation transmission properties may be employed.

Alternate coil arrangements of the conduit means about elongated radiation producing tube 26 can also be employed using the teaching of the present invention and without departing from the scope of the present invention. One such alternate configuration is wrapping the tube means longitudinally about elongated radiation producing tube 26, as opposed to an axial wrap, as shown in FIGS. 1 and 2. Such a configuration is illustrated by FIG. 10 of the drawings. Separate tube means 40 and 41 extend longitudinally along the ultraviolet producing tube 26 in a serpentine fashion, each tube means occupying a respective 180° arc.

Another alternate configuration is shown in FIGS. 11 through 13. A cylindrically shaped jacket 43 surrounds the ultraviolet producing tube 26. The jacket 43 is divided diametrically into two separate, non-communicative half-jackets 44 and 45, through which the fluid flows.

Each half-jacket 44 and 45 includes baffle means to provide a serpentine, turbulent flow to the fluid. The baffle means may be a series of partition walls 46 arranged in spaced apart relationship longitudinally along the half-jackets 44, 45, with alternately spaced walls 46 joined to and extending inwardly from opposite sides of its respective half-jacket. Each wall 46 does not extend entirely from one opposite side of the half-jacket 44, 45 to the other, so as to allow fluid to flow through the half-jackets. Thus, the partition walls 46 provide a tortuous path for the fluid, which maximizes the exposure of microorganisms and bacteria carried by the fluid to ultraviolet radiation emitted by the tube 26.

Figure 14:
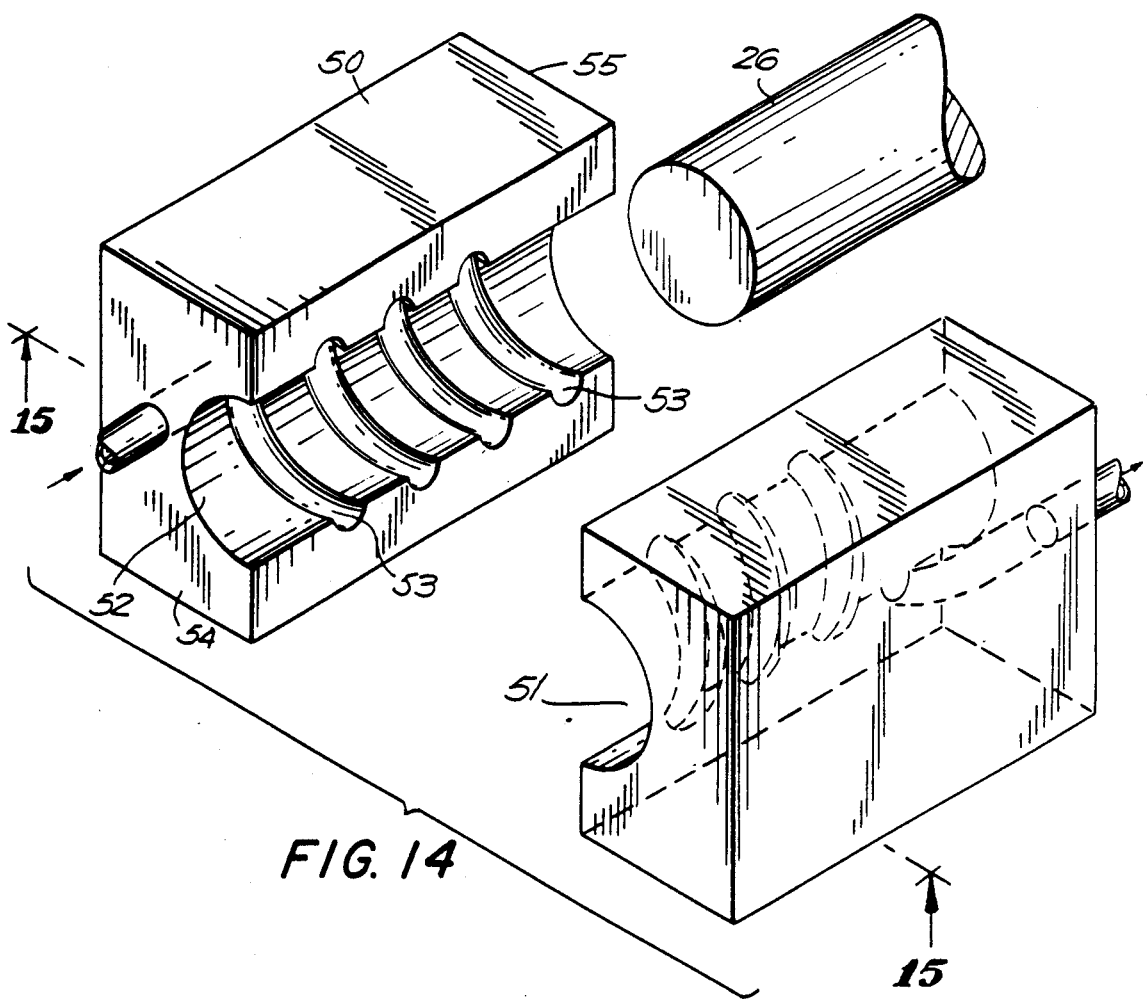
FIG. 14 is a partial, exploded view of a fourth embodiment of the present invention.
Figure 15:
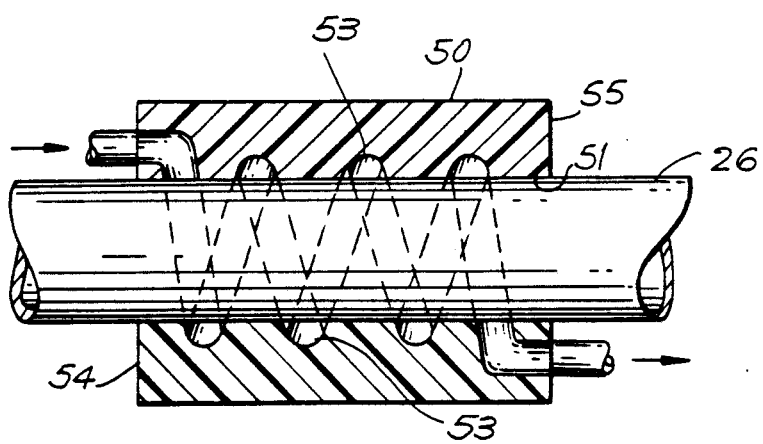
FIG. 15 is a sectional view of the embodiment shown in FIG. 14 taken along the lines 15—15 of FIG. 14.

A further alternate conduit means is illustrated by FIGS. 14 and 15. A fluid impervious core 50 has formed therein a central bore 51 running longitudinally through it. The bore 51 is dimensioned to closely receive the ultraviolet producing tube member 26, which is preferably cylindrical in shape. Formed in the inner surface 52 of the core 50 defining the bore 51 is a continuous groove 53, which is preferably semi-circular in cross-section. The groove 53 extends spirally in the inner surface of the core 50, from one axial end 54 of the core to the opposite axial end 55. The ultraviolet tube member 26 is so tightly received by the bore of the core that it defines with the grooved inner surface a spiral flow channel for fluid passage surrounding the ultraviolet tube member 26.

A further embodiment of the present invention is illustrated by FIG. 15. If desired, the tube members need not be interleaved, as shown in FIG. 1. Rather, separate spirally wound tube members 60, 61 may be wrapped about the ultraviolet radiation producing tube 26 and coaxially positioned adjacent to each other, end to end. Each tube member 60, 61 preferably encircles one half of the ultraviolet tube's length.

In accordance with the present invention, a fluid flowcontrol system is constructed to receive the incoming fluid and pass the fluid through an ultraviolet radiation exposure prior to delivering the fluid to a filter. In addition, after filtration, the fluid is again exposed to ultraviolet radiation immediately prior to delivering the fluid directly to the user. By employing the fluid purification system of the present invention, potable water, virtually free of all bacteria, odor, chloroform, inorganic particulate matter, organic matter and live microorganisms, is provided.

Furthermore, by employing the present invention, a fluid purification system is realized with which previously unreachable goals are attained in a system which is compact and easily positioned and interconnected to existing water or other fluid supply systems. One major aspect of attaining this compact system is the use of a single ultraviolet radiation producing tube about which is tightly coiled the fluid flow controlling conduit means, which provide both fluid flow into the filter means as well as fluid flow out of the filter means. This compact arrangement is further enhanced by the continuous interleaving of the two independent tube means which form the conduit means. In this way, using a single ultraviolet radiation producing tube, the requisite dual exposure to ultraviolet radiation is attached with simplicity, in a minimum, compact size.

As is apparent from the preceding detailed description of the preferred embodiments, the fluid purification system of the present invention continuously produces potable water, virtually free of all live microorganisms, for immediate use, both consistently and for longer time intervals than obtained with conventional systems. It is believed that the efficacy of the system of this invention is due principally to its dual exposure of the fluid to ultraviolet radiation prior to filtration and after filtration, and the maximization of exposure of the microorganisms to the ultraviolet radiation producing tube. By employing this invention, the filter is isolated from bacteria contamination, since both its inlet and outlet ports are connected directly to the ultraviolet radiation exposure zones.

As a result of this unique configuration, live microorganisms do not enter the filter medium from the incoming fluid, since virtually all of the microorganisms in the fluid are killed during the initial ultraviolet radiation exposure. Similarly, microorganisms cannot enter the filter medium from the output side, since the output cf the filter medium is connected directly to the second treatment zone of ultraviolet radiation.

It is believed that by employing this dual radiation exposure construction with its resulting filter isolation, a filter previously contaminated by bacteria or other microorganisms will eventually be completely cleaned of all live microorganisms.

It has been found that although the filter medium, in particular activated charcoal, is a breeding ground for microorganisms, the microorganisms require a constant supply of new microorganisms in order to maintain a complete growth pattern. However, in the present invention, the filter is isolated, and live microorganisms are incapable of entering the filter, either from the input side or the output side. Consequently, microorganisms originally present in the filter medium die, and the filter ultimately becomes virtually bacteria-free and is maintained virtually bacteria-free, since live microorganisms are continuously prevented from entering the filter medium.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for purifying liquids comprising the steps of:
   supplying a liquid to be purified to a purifier inlet;
   exposing said liquid to be purified substantially immediately upon entering said inlet to a predetermined quantity of ultraviolet radiation;
   passing the ultraviolet-radiated liquid through a liquid purification filter;
   exposing the filtered liquid to a further predetermined quantity of ultraviolet radiation, said further ultraviolet radiation being provided to said liquid until said liquid is delivered to a purifier outlet for use;
   providing an ultraviolet radiation transparent, helically coiled, conduit arrangement for passing said liquid from said inlet to said filter and from said filter to said outlet;
   selecting said predetermined quantity of ultraviolet radiation and the size of said conduit arrangement to assure the extinction of undesirable microorganism, bacteria and viruses in said liquid; and
   isolating the liquid after entry in said purifier inlet up to delivery to said purifier outlet from an external contamination source.

2. A method for purifying liquids comprising the steps of:
   supplying a liquid to be purified to a purifier inlet;
   exposing said liquid to be purified substantially immediately upon entering said inlet to a predetermined quantity of ultraviolet radiation;
   passing the ultraviolet-radiated liquid through a liquid purification filter;
   exposing the filtered liquid to a further predetermined quantity of ultraviolet radiation;
   repeating the above steps in the recited sequence a predetermined number of times and wherein, in the final exposing step, the further ultraviolet radiation is provided to said liquid until said liquid is delivered to a purifier outlet for use;
   providing an ultraviolet radiation transparent, helically coiled, conduit arrangement for passing said liquid from said inlet to said filter and from said filter to said outlet;
   selecting said predetermined quantity of ultraviolet radiation and the size of said conduit arrangement to assure the extinction of undesirable microorganisms, bacteria and viruses in said liquid; and
   isolating the liquid after entry to said purifier inlet up to delivery to said purifier output from any external contamination source.

3. A liquid sterilization system comprising:
   means for providing emitted radiation including an elongated ultraviolet radiation emitting tube coupled to a source of electrical energy for emitting ultraviolet radiation; and
   a pair of tubular liquid conduits, said conduits being helically coiled in paired manner about said ultraviolet radiation emitting tube from one end of said tube to the other with each coil of said helically coiled conduits laterally abutting adjacent coils to peripherally surround substantially the entire length of said tube, each of said conduits having an inlet port at one end and an outlet port at the other and, said conduits being transparent to ultraviolet radiation to allow exposure of liquid flowing through said conduits to ultraviolet radiation emitted by said tube;
   the size of said means for providing emitted radiation and the size of said conduits chosen to assure extinction of undesirable microorganisms, bacteria and viruses in liquid flowing through said conduits.

4. The system of claim 3 wherein said conduits being helically coiled in paired manner about said tube are arranged such that the coils of one conduit lie between coils of the other conduit except for the outermost coils at each end.

5. The system of claims 3 wherein the inlet port of one conduit is paired with and immediately adjacent to the outlet port of the other conduit to allow for opposing flow of liquid through said conduits.

6. The system of claim 3 including means to couple the outlet of one conduit to the inlet of the other conduit, said coupling means being arranged to prevent entry of external contamination to said system.

7. The system of claim 6 wherein said coupling means includes means to couple the outlet of said one conduit to the inlet of the other conduit through a further liquid processing means.

8. The system of claim 3 wherein said conduits are composed of plastic and are cylindrical in cross section.

9. A liquid purification system comprising:
   an inlet to said system for supply of liquid to be purified;
   means for emitting ultraviolet radiation;
   a first conduit directly connected at one end thereof to said inlet for receiving the liquid to be purified, said first conduit having an outlet port at the other end and being transparent to the ultraviolet radiation emitted by said means for allowing said ultraviolet radiation to impinge on the liquid throughout flow of the liquid through first conduit;
   liquid processing means, coupled to said outlet port of said first conduits for processing the irradiated liquid and for bringing it to an outlet of said processing means after processing;
   a second conduit connected at one end thereof to said processing means outlet for receiving the processed liquid, said second conduit having an outlet port at the other end and being transparent to the ultraviolet radiation emitted by said source for allowing said ultraviolet radiation to impinge on the processed liquid throughout flow of the liquid through said second conduit to the outlet port of said second conduit and a system outlet directly connected to said outlet port of said second conduit for delivering purified liquid to a user, said system being arranged from inlet to outlet so as to prevent entry of external sources of contamination;
   said first and second conduits being helically wound about said ultraviolet radiation emitting means and said first and second conduits and said ultraviolet radiation emitting means having such size to assure the extinction of undesirable microorganisms, bacteria and viruses in the liquid upon exposure to said ultraviolet energy.

10. The system of claim 9 wherein said source of ultraviolet radiation is an elongated tube coupled to a source of electrical energy for emitting ultraviolet radiation.

11. The purification system of claim 10 wherein said conduits are wound about said elongated tube in a tortuous manner so as to provide substantial exposure of liquid flowing through said conduits to ultraviolet radiation and for providing turbulence to liquid flowing through said conduits to assure that the liquid passing therethrough is thoroughly exposed to said ultraviolet radiation.

12. The purification system of claim 11 wherein said first and second conduits are helically coiled in paired manner about said ultraviolet radiation emitting tube from one end of said tube to the other with each coil of said helically coiled conduits laterally abutting adjacent coils to peripherally surround substantially the entire length of said tube.

13. The liquid purification system of claim 11 wherein said first and second conduits are helically coiled in sequential manner about substantially the entire length of said ultraviolet radiation emitting tube, each coil of said conduits laterally abutting adjacent coils.

14. The liquid purification system of claim 9 wherein said liquid processing means is a filter.

15. A modular liquid purification system comprising:
a system inlet;
a system outlet;
a number of modular liquid sterilization systems, each having:
means for providing emitted radiation including an elongated radiation emitting tube coupled to a source of electrical energy for emitting ultraviolet radiation and a pair of tubular conduits, said conduits being helically coiled in paired manner about said ultraviolet radiation emitting tube from one end of said tube to the other with each coil of said helically coiled conduits laterally abutting adjacent coils to peripherally surround substantially the entire length of said tube, each of said conduits having an inlet port at one end and an outlet port at the other end, said conduits being transparent to ultraviolet radiation to allow exposure of liquid flowing through said conduits to ultraviolet radiation and wherein the inlet port of one conduit is paired with and immediately adjacent to the outlet port of the other conduit to allow for opposing flow of liquid through said conduits; a number of modular filter systems for filtering incoming fluid, each filter system having a filter inlet and a filter outlet; and means for interconnecting said number of liquid sterilization systems and said number of filter systems for providing a liquid purification system having a closed liquid path from system inlet to system outlet and for having fluid supplies to said systems only following exposure to ultraviolet radiation and for having fluid filtered by said filter systems always subject to exposure to ultraviolet radiation;

the size of said means for providing emitted radiation and the size of said conduits chosen to assure extinction of undesirable microorganisms, bacteria and viruses in liquid flowing through said conduits.

16. The modular liquid purification system of claim 15 including at least two of said sterilization systems and one said filter system, said one conduits of said sterilization systems being connected in series, said other conduits of said sterilization systems being connected in series and said filter system being connected between the said two series connections.

17. The modular liquid purification system of claim 15, including at least two of said sterilization systems and at least two of said filter systems, each sterilization system having one of said filter systems being connected between two conduits thereof, each sterilization system and filter system forming a first and second liquid purification system, wherein liquid purified by said first purification system is supplied to said second purification system for further purification prior to delivery to said system outlet.

* * * * *